(12) United States Patent
Wood

(10) Patent No.: US 11,712,258 B2
(45) Date of Patent: Aug. 1, 2023

(54) TISSUE RESECTION SYSTEMS INCLUDING FLUID OUTFLOW MANAGEMENT

(71) Applicant: COVIDIEN LP, Mansfield, MA (US)

(72) Inventor: Timothy J. Wood, Wilmington, MA (US)

(73) Assignee: Covidien LP, Mansfield, MA (US)

( * ) Notice: Subject to any disclaimer, the term of this patent is extended or adjusted under 35 U.S.C. 154(b) by 858 days.

(21) Appl. No.: 16/214,852

(22) Filed: Dec. 10, 2018

(65) Prior Publication Data

US 2020/0179576 A1  Jun. 11, 2020

(51) Int. Cl.
*A61B 17/32* (2006.01)
*A61M 1/00* (2006.01)
*A61B 17/00* (2006.01)

(52) U.S. Cl.
CPC ......... *A61B 17/32002* (2013.01); *A61M 1/60* (2021.05); *A61M 1/743* (2021.05); *A61M 1/76* (2021.05); *A61M 1/777* (2021.05); *A61B 2017/00199* (2013.01); *A61B 2217/005* (2013.01); *A61B 2217/007* (2013.01); *A61M 1/74* (2021.05); *A61M 1/78* (2021.05)

(58) Field of Classification Search
CPC ...... A61M 1/774; A61M 1/0058; A61M 1/76; A61M 1/77; A61M 1/00; A61M 1/0023; A61M 1/84; A61M 1/86; A61M 3/0202; A61M 2205/128; A61B 1/00068; A61B 2217/005; A61B 2217/007; A61B 1/12; A61B 1/015; A61B 2218/00; A61B 2218/001; A61B 2218/002; A61B 2218/007
See application file for complete search history.

(56) References Cited

U.S. PATENT DOCUMENTS

| | | | |
|---|---|---|---|
| 5,460,490 A | 10/1995 | Carr et al. | |
| 6,224,617 B1 | 5/2001 | Saadat et al. | |
| 7,597,662 B2 | 10/2009 | Litscher et al. | |
| 9,943,639 B2 | 4/2018 | Germain et al. | |
| 2003/0146299 A1* | 8/2003 | Suzuki | A61M 1/0062 239/310 |
| 2010/0249693 A1* | 9/2010 | Links | A61F 9/007 604/22 |
| 2015/0182105 A1* | 7/2015 | Salman | A61B 1/00137 600/104 |
| 2015/0359666 A1* | 12/2015 | Zacharias | A61M 1/842 604/500 |
| 2016/0166742 A1* | 6/2016 | Layser | A61M 1/742 604/31 |
| 2016/0220751 A1* | 8/2016 | Mallough | A61F 9/00745 |
| 2016/0346123 A1* | 12/2016 | Koplin | A61M 3/0216 |

(Continued)

*Primary Examiner* — Adam Marcetich
*Assistant Examiner* — Meagan Ngo
(74) *Attorney, Agent, or Firm* — Carter, DeLuca & Farrell LLP

(57) ABSTRACT

A surgical system includes a surgical instrument, a collection canister, outflow tubing coupled between the surgical instrument and the collection canister to define an outflow path from the surgical instrument to the collection canister, and a control console. The outflow tubing includes a valve module including a controllable valve disposed within the outflow path to selectively control flow therealong. The control console is configured to control operation of the surgical instrument and to control the controllable valve.

14 Claims, 6 Drawing Sheets

(56) References Cited

U.S. PATENT DOCUMENTS

2017/0087012 A1\* 3/2017 Kato .................. F04B 43/1292
2017/0172796 A1   6/2017 Biancalana et al.
2019/0099548 A1\* 4/2019 Mehta ................. A61M 3/0216
2019/0133822 A1\* 5/2019 Banko ................. A61M 1/0058

\* cited by examiner

TISSUE RESECTION SYSTEMS INCLUDING FLUID OUTFLOW MANAGEMENT

BACKGROUND

1. Technical Field

The present disclosure relates generally to surgical systems and, more particularly, tissue resection systems including fluid outflow management.

2. Background of Related Art

Surgical procedures, such as tissue resection procedures, may be performed endoscopically within an organ, such as a uterus, by inserting an endoscope into the uterus and passing a tissue resection device through the endoscope and into the uterus. With respect to such endoscopic tissue resection procedures, it often is desirable to distend the uterus with a fluid, for example, saline, sorbitol, or glycine. The inflow and outflow of the fluid during the procedure maintains the uterus in a distended state and flushes tissue and other debris from within the uterus to maintain a visible working space.

SUMMARY

As used herein, the term "distal" refers to the portion that is described which is further from a user, while the term "proximal" refers to the portion that is described which is closer to a user. Further, to the extent consistent, any or all of the aspects described herein may be used in conjunction with any or all of the other aspects described herein.

Provided in accordance with aspects of the present disclosure is a surgical system including a surgical instrument, a collection canister, outflow tubing coupled between the surgical instrument and the collection canister to define an outflow path from the surgical instrument to the collection canister, and a control console. The outflow tubing includes a valve module including a controllable valve disposed within the outflow path to selectively control flow thereralong. The control console is configured to control operation of the surgical instrument and to control the controllable valve.

In an aspect of the present disclosure, the surgical instrument includes a module dock configured to releasably engage the valve module. In such aspects, the control console may be configured to control the controllable valve via the module dock of the surgical instrument.

In another aspect of the present disclosure, the valve module further includes a communication device and the module dock is configured to retrieve information from the communication device upon engagement of the valve module with the module dock.

In another aspect of the present disclosure, the control console includes a module dock configured to releasably engage the valve module. In such aspects, the control console may be configured to control the controllable valve via the module dock.

In still another aspect of the present disclosure, the valve module further includes a communication device and wherein the module dock is configured to retrieve information from the communication device upon engagement of the valve module with the module dock.

In yet another aspect of the present disclosure, the surgical instrument includes an end effector assembly including a first communication device and a handpiece including a second communication device. The end effector assembly is configured to releasably engage the handpiece and, when the end effector assembly is engaged with the handpiece, the second communication device is configured to retrieve information from the first communication device.

In still yet another aspect of the present disclosure, the surgical instrument includes an end effector assembly and a handpiece, and wherein an outflow fluid path of the surgical instrument to the outflow tubing extends through the end effector assembly and is isolated from the handpiece.

In another aspect of the present disclosure, the surgical instrument includes an end effector assembly and a handpiece, and wherein an outflow fluid path of the surgical instrument to the outflow tubing extends through the end effector assembly and the handpiece.

In yet another aspect of the present disclosure, vacuum tubing is coupled between the control console and the collection canister.

In still another aspect of the present disclosure, the outflow tubing includes a distal tube portion connected between the surgical instrument and the valve module and a proximal tubing portion connected between the valve module and the collection canister.

In another aspect of the present disclosure, the valve module further includes an inflow port and a vacuum port. In such aspects, the proximal tubing portion may define first and second isolated flow paths, the first isolated flow path defined between the inflow port and the collection canister and the second isolated flow path defined between the vacuum port and the collection canister.

Another surgical system provided in accordance with aspects of the present disclosure includes a surgical instrument, a control console configured to control operation of the surgical instrument, a valve and collection module configured to releasably mount to the control console, and outflow tubing. The valve and collection module includes a controllable valve and a collection reservoir. The outflow tubing is coupled between the surgical instrument and the collection reservoir of the valve and collection module to define an outflow path from the surgical instrument to the collection reservoir. The controllable valve is disposed within the outflow path to selectively control flow thereralong.

In an aspect of the present disclosure, the control console is configured to control the controllable valve.

In another aspect of the present disclosure, the control console includes a module dock configured to releasably engage the valve and collection module.

In another aspect of the present disclosure, the valve and collection module further includes a communication device. In such aspects, the module dock may be configured to retrieve information from the communication device upon engagement of the valve and collection module with the module dock.

In yet another aspect of the present disclosure, the valve and collection module further includes a vacuum port configured to couple to a vacuum source of the control console.

In still another aspect of the present disclosure, the valve and collection module further includes a barrier disposed between the vacuum port and the collection reservoir.

In still yet another aspect of the present disclosure, the valve and collection module further includes a one-way valve disposed between the outflow tubing and the collection reservoir.

In another aspect of the present disclosure, the surgical instrument includes an end effector assembly and a handpiece, and an outflow fluid path of the surgical instrument to the outflow tubing extends through the end effector assembly and is isolated from the handpiece.

In another aspect of the present disclosure, the surgical instrument includes an end effector assembly and a handpiece, and an outflow fluid path of the surgical instrument to the outflow tubing extends through the end effector assembly and the handpiece.

BRIEF DESCRIPTION OF THE DRAWINGS

Various aspects and features of the present disclosure are described hereinbelow with reference to the drawings wherein like numerals designate identical or corresponding elements in each of the several views.

DETAILED DESCRIPTION

Figure 1:
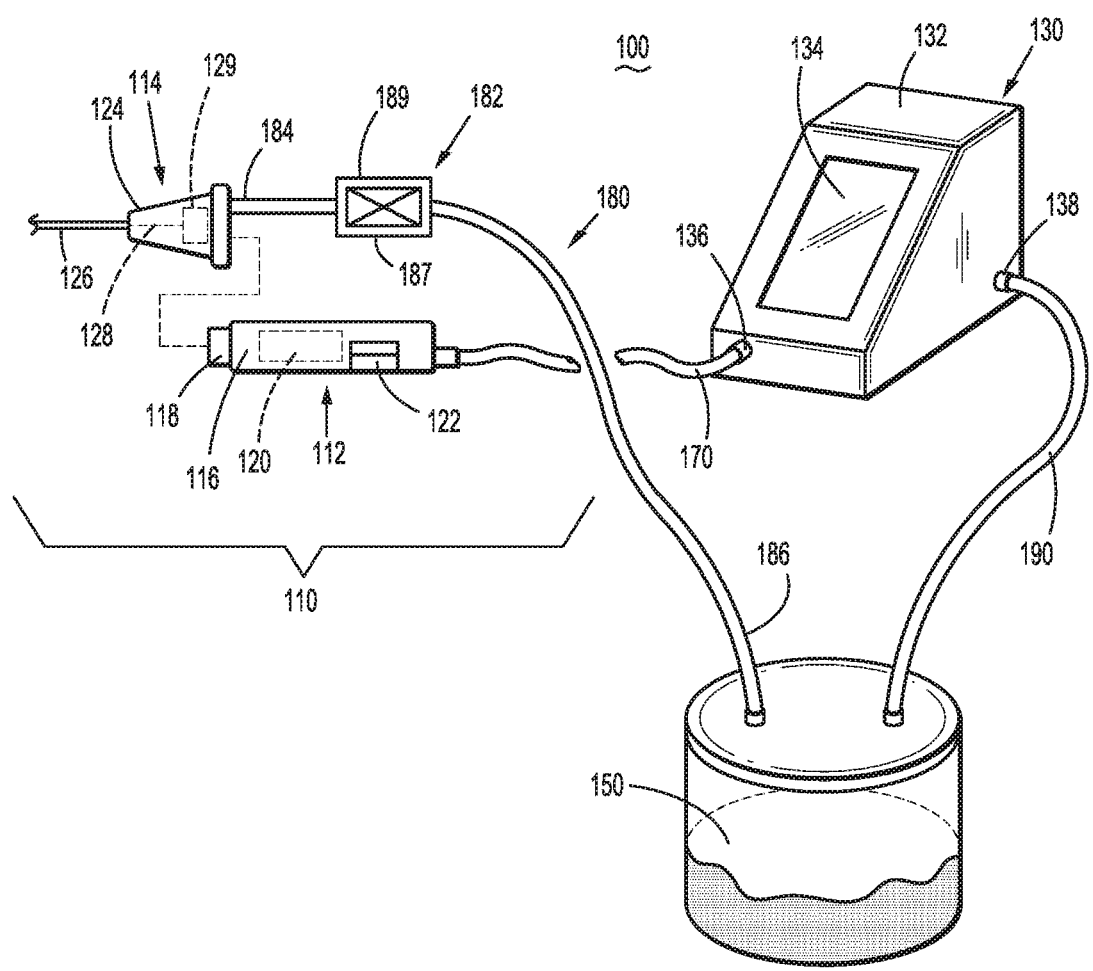
FIG. 1 is a perspective view of a surgical system provided in accordance with aspects of the present disclosure.

Referring to FIG. 1 a surgical system provided in accordance with aspects of the present disclosure is shown generally identified by reference numeral 100. Surgical system 100 generally includes a surgical instrument 110, a control console 130, and a collection canister 150. Surgical system 100 further includes a cable 170, outflow tubing 180, and vacuum tubing 190.

Surgical instrument 110 includes a handpiece 112 that may be configured as a reusable component and an end effector assembly 114 that may be configured as a single-use, disposable component. Handpiece 112 includes a housing 116 to facilitate grasping and manipulation of surgical instrument 110 by a user. Handpiece 112 further includes an output interface 118 configured to operably engage end effector assembly 114, a motor 120 disposed within housing 116 and operably coupled to output interface 118 to drive output interface 118 and, thus, drive end effector assembly 114, and a module dock 122 configured to mechanically engage and electrically coupled to a valve module 182 associated with outflow tubing 180, as detailed below. Cable 170 electrically couples handpiece 112 and control console 130 with one another and, more specifically, electrically couples control console 130 with motor 120 to power and control operation of motor 120 and electrically couples control console 130 with valve module 182 to enable communication of, for example, identification, setting, and control information therebetween. In embodiments, cable 170 is fixedly attached to handpiece 112 and releasably couplable with control console 130, although other configurations are also contemplated.

End effector assembly 114 includes a proximal hub 124 configured to releasably engage housing 116 of handpiece 112 to releasably mechanically engage end effector assembly 114 with handpiece 112. End effector assembly 114 further includes an outer shaft 126 extending distally from proximal hub 124 and a cutting shaft 128 extending through outer shaft 126. A proximal end of cutting shaft 128 extends into proximal hub 124 wherein an input interface 129 is engaged with cutting shaft 128. Input interface 129 is configured to operably couple to output interface 118 of handpiece 112 when proximal hub 124 is engaged with housing 116 such that, when motor 120 is activated to drive output interface 118, input interface 129 is driven in a corresponding manner to thereby move cutting shaft 128 within and relative to outer shaft 126.

Outer shaft 126, as noted above, extends distally from proximal hub 124 and, in embodiments, is stationary relative to proximal hub 124, although other configurations are also contemplated. Outer shaft 126 may define a window (not shown) through a side wall thereof towards a distal end thereof to provide access to cutting shaft 128 which is rotatably and/or translatably disposed within outer shaft 126. Cutting shaft 128 may define an opening (not shown) towards the distal end thereof providing access to the interior thereof and may include a serrated cutting edge (not shown) surrounding the opening, although other suitable cutting edge configurations are also contemplated. Alternatively, or additionally, outer shaft 126 may include a cutting edge defined about the window thereof.

Motor 120, as noted above, is activated to move cutting shaft 128 and, more specifically, to drive rotation and/or translation of cutting shaft 128 relative to outer shaft 126. Control console 130, coupled to motor 120 via cable 170, enables selective powering and controlling of motor 120 and, thus, selective rotation and/or translation of cutting shaft 128 relative to outer shaft 126 to resect tissue adjacent the distal end of end effector assembly 114.

Continuing with reference to FIG. 1, a distal end 184 of outflow tubing 180 is coupled to proximal hub 124 of end effector assembly 114 in fluid communication with the interior of cutting shaft 128 and/or the interior of outer shaft 126 such that fluid, tissue, and debris drawn into cutting shaft 128 and/or outer shaft 126 may be suctioned, under vacuum, through end effector assembly 114 and outflow tubing 180. A proximal end 186 of outflow tubing 180 is coupled to collection canister 150 to enable the fluid, tissue, and debris suctioned through end effector assembly 114 and outflow tubing 180 to be deposited within collection canister 150. Distal end 184 of outflow tubing 180 may be fixedly secured to proximal hub 124 while proximal end 186 of outflow tubing 180 is configured to releasably couple to collection canister 150, although other configurations are also contemplated.

Outflow tubing 180 further includes, as noted above, a valve module 182. Valve module 182 is disposed between distal and proximal ends 184, 186, respectively, of outflow tubing 180. Valve module 182 includes a controllable valve 187 disposed within the flow path defined through outflow tubing 180 to selectively permit and inhibit flow therethrough and/or to control the flow rate therethrough, and a communication device 189, e.g., a RFID tag, storing information regarding end effector assembly 114 such as, for example, identifying information, use setting information, etc. Valve module 182 is configured for releasable engagement with module dock 122 of handpiece in electrical communication therewith. With valve module 182 engaged with module dock 122 and, as detailed above, module dock 122 coupled to control console 130 via cable 170, the information stored on communication device 189 of valve module 182 may be communicated to control console 130 (via a communication receiver, e.g., an RFID reader, of module dock 122 and cable 170) for use in controlling motor 120 to drive end effector assembly 114 in accordance with the settings, parameters, and/or other configuration thereof, and/or to control controllable valve 187 in an appropriate manner, e.g., in accordance with the activation/deactivation of motor 120, the position and/or orientation of cutting shaft 128, or in any other suitable manner. Thus, end effector assemblies 114 of various different configuration (different length, diameter, cutting arrangement, outflow tube configuration, etc.) may be utilized with handpiece 112 and control console 130 in a plug-and-play manner.

Referring still to FIG. 1, collection canister 150, as noted above, is coupled to proximal end 186 of outflow tubing 180 to receive the fluid, tissue, and debris suctioned through end effector assembly 114 and outflow tubing 180. Vacuum tubing 190 is coupled between collection canister 150 and a vacuum source (not shown) disposed within or otherwise associated with control console 130 such that, upon activation of the vacuum source, negative pressure is established through collection canister 150, outflow tubing 180, and the interior of cutting shaft 128 and/or outer shaft 126 of end effector assembly 114 to draw the fluids, tissue, and debris into and through cutting shaft 128 and/or outer shaft 126, outflow tubing 180, and into collection canister 150.

Control console 130, as noted above, is configured to receive information from communication device 189 of valve module 182 and, based at least in part on that information, control motor 120 of handpiece 112, control controllable valve 187 of valve module 182, and operate the vacuum source thereof to resect tissue and suction resected tissue, fluid, and debris through end effector assembly 114 and outflow tubing 180 for depositing into collection canister 150. Control console 130 generally includes an outer housing 132, a touch-screen display 134 accessible from the exterior of outer housing 132, a cable port 136 configured to receive cable 170, and a vacuum tube port 138 configured to receive vacuum tube 190. Outer housing 132 houses internal electronics (not shown) as well as the vacuum source. Control console 130 may be configured to connect to a mains power supply (not shown) for powering control console 130. Further, control console 130 may be configured to receive user input, e.g., use information, setting selections, etc., via touch-screen display 134 or a peripheral input device (not shown) coupled to control console 130. Operational input, e.g., ON/OFF signals, power level settings (HI power vs. LO power), etc., may likewise be input via touch-screen display 134 or a peripheral input device (not shown) such as, for example, a footswitch (not shown), a handswitch (not shown) disposed on handpiece 112, etc.

In preparation for use, end effector assembly 114 is engaged with handpiece 112, valve module 182 is engaged within module dock 122, cable 170 is coupled to control console 130 (and handpiece 112 if not already connected thereto), proximal end 186 of outflow tubing 180 is coupled to collection canister 150 (and distal end 184 thereof to end effector assembly 114 if not already connected thereto), and vacuum tubing 190 is coupled between vacuum tube input 138 of control console 130 and collection canister 150. The connections between valve module 182 and module dock 122 and between cable 170 and control console 130, as detailed above, enable communication of information regarding end effector assembly 114 (and, in embodiments, outflow tubing 180) to control console 130 to enable control console 130 to adjust setting information, use parameters, etc., based thereupon.

In use, upon an activation input provided to control console 130, control console 130 powers and controls motor 120 of handpiece 112 to, in turn, drive cutting shaft 128 of end effector assembly 114 to resect tissue adjacent the distal end of end effector assembly 114. During activation, control console 130 also controls controllable valve 187 and the vacuum source disposed within control console 130 to suction fluid, the resected tissue, and debris through cutting shaft 128 and/or outer shaft 126, outflow tubing 180, and into collection canister 150.

As demonstrated above, surgical system 100 provides a configuration whereby handpiece 112 and control console 130 remain isolated from the fluid, tissue, and debris suctioned through surgical instrument 110 and into collection canister 150, thus facilitating the cleaning process for reuse of handpiece 112 and control console 130. More specifically, while valve module 182 is coupled to module dock 122, module dock 122 communicates signals (electrical and/or mechanical) to control controllable valve 187 of valve module 182 without requiring contact with the flow path through outflow tubing 180 and/or controllable valve 187. End effector assembly 114 and outflow tubing 180, on the other hand, may together be configured as a single-use component that is discarded after use.

Figure 2:
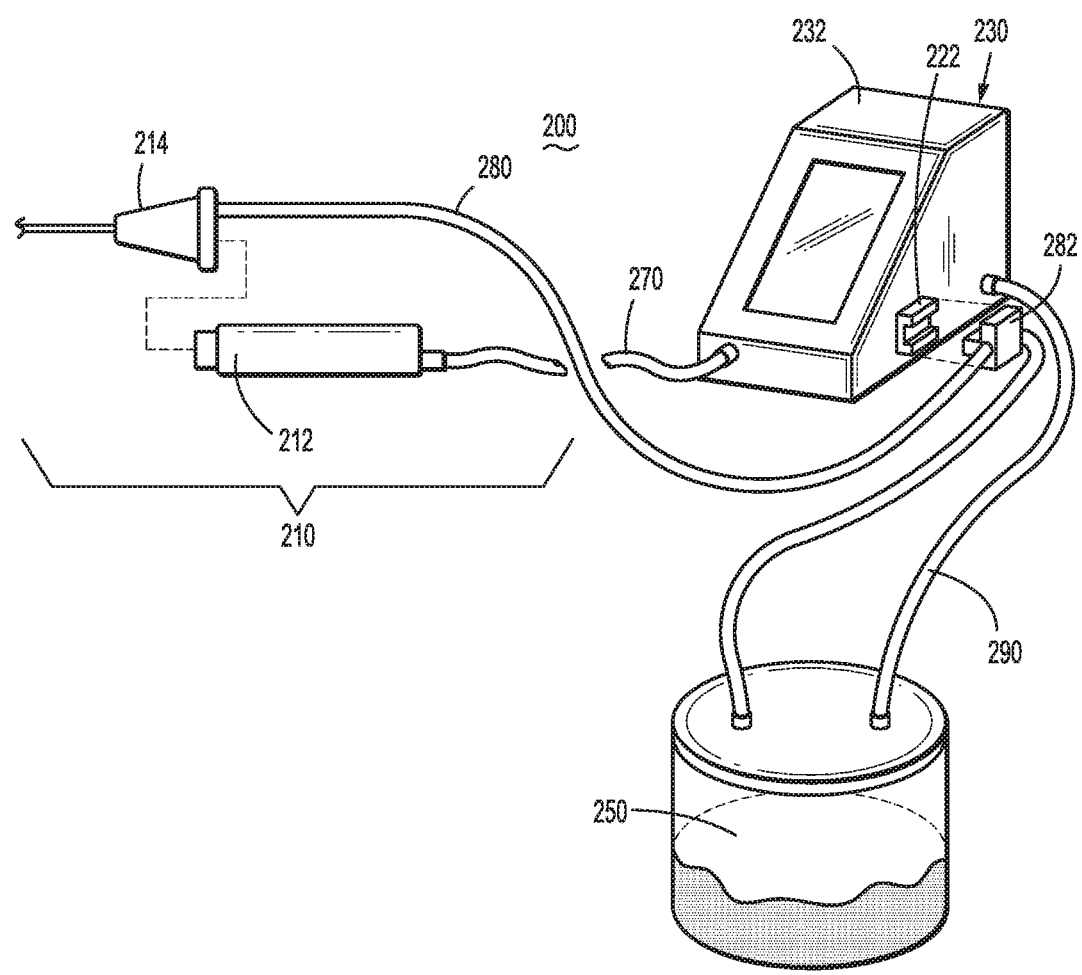
FIG. 2 is a perspective view of another surgical system provided in accordance with aspects of the present disclosure.

Turning now to FIG. 2, another surgical system provided in accordance with aspects of the present disclosure is shown generally identified by reference numeral 200. Surgical system 200 generally includes a surgical instrument 210, a control console 230, and a collection canister 250. Surgical system 200 further includes a cable 270, outflow tubing 280, and vacuum tubing 290. Surgical system 200 is similar to and may include any of the features of surgical system 100 (FIG. 1) except as specifically contradicted below. Thus, for purposes of brevity, only the differences between surgical system 200 and surgical system 100 (FIG. 1) are described in detail below.

Control console 230 of surgical system 200 includes a module dock 222 disposed on outer housing 232 thereof. That is, rather than module dock 222 provided on handpiece 212 of surgical instrument 210 as in surgical system 100 (FIG. 1), module dock 222 is disposed on outer housing 232 of control console 230. Valve module 282 of outflow tubing 280 of surgical system 200 is configured for releasable engagement with module dock 222 in electrical communication therewith. With valve module 282 engaged with module dock 222, the information stored on the communication device (not shown) of valve module 282 may be communicated to control console 230 (via a communication receiver, e.g., an RFID reader, of module dock 222) for use in controlling the motor (not shown) of handpiece 212 to drive end effector assembly 214 in accordance with the settings, parameters, and/or other configuration thereof, and/or to control the controllable valve (not shown) of valve module 282 in an appropriate manner, e.g., in accordance with the activation/deactivation of the motor of handpiece 212, the position and/or orientation of the cutting shaft (not shown) of end effector assembly 214, or in any other suitable manner.

Similarly, as with surgical system 100 (FIG. 1), surgical system 200 provides a configuration whereby handpiece 212 and control console 230 remain isolated from the fluid, tissue, and debris suctioned through surgical instrument 210 and into collection canister 250. Further, relocating module dock 222 to control console 230 eliminates the need to provide module dock 222 and any associated components on handpiece 212 and/or through cable 270.

Figure 3:
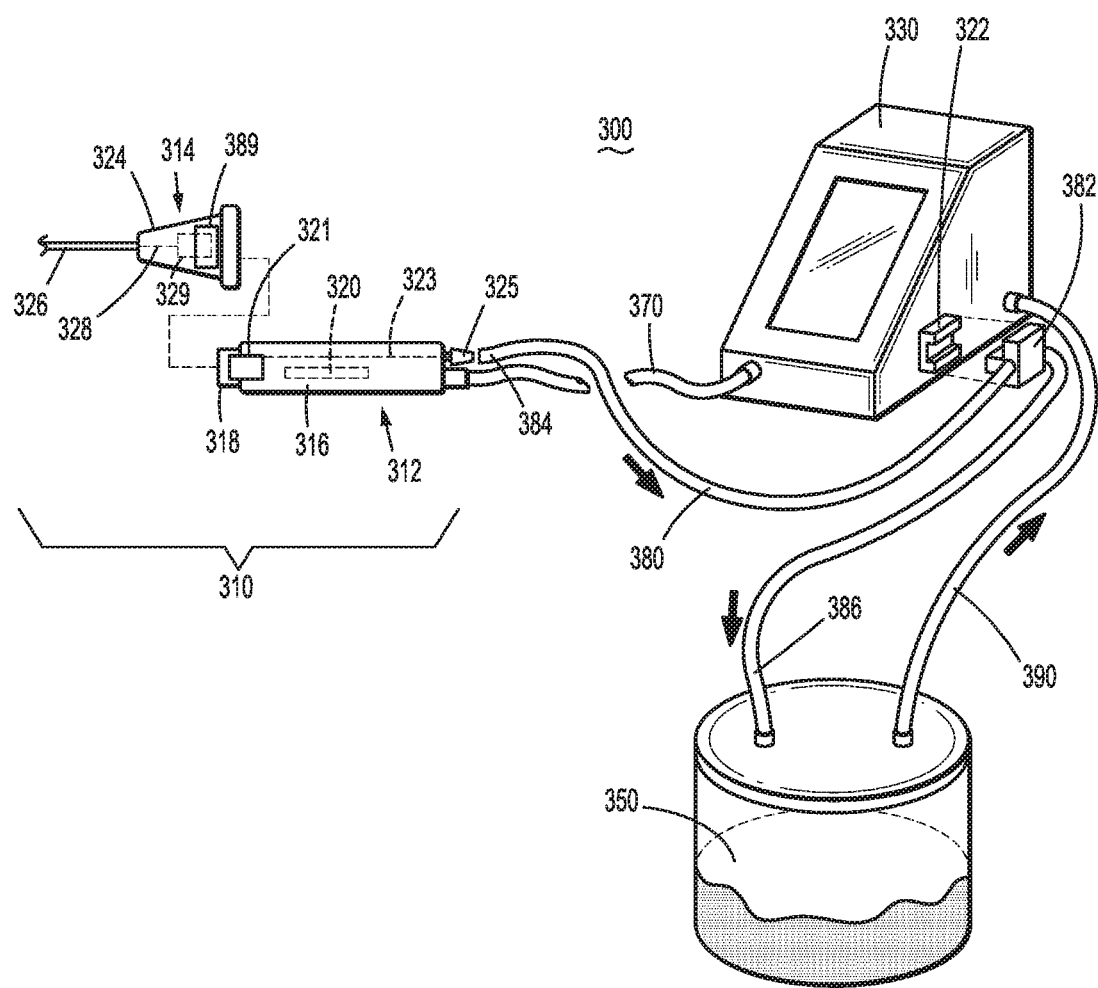
FIG. 3 is a perspective view of still another surgical system provided in accordance with aspects of the present disclosure.

Referring to FIG. 3, another surgical system provided in accordance with aspects of the present disclosure is shown generally identified by reference numeral 300. Surgical system 300 generally includes a surgical instrument 310, a control console 330, and a collection canister 350. Surgical system 300 further includes a cable 370, outflow tubing 380, and vacuum tubing 390. Surgical system 300 is similar to and may include any of the features of surgical systems 100, 200 (FIGS. 1 and 2) except as specifically contradicted below. For purposes of brevity, only the differences between surgical system 300 and surgical system 100 (FIG. 1) are described in detail below.

Surgical instrument 310, similarly as with surgical instruments 110, 210 (FIGS. 1 and 2, respectively) includes a handpiece 312 and an end effector assembly 314. Handpiece 312 includes a housing 316, an output interface 318, a motor 320, and further includes a communication receiver 321, e.g., an RFID reader, operably disposed on or within housing 316 and a flow lumen 323 extending through housing 316 and communicating with a proximal connector 325. Cable 370 electrically couples handpiece 312 and control console 330 with one another and, more specifically, electrically couples control console 330 with motor 320 to power and control operation of motor 320 and electrically couples control console 330 with communication receiver 321 to enable communication of, for example, identification, setting, and control information therebetween.

End effector assembly 314 includes a proximal hub 324 configured to releasably engage housing 316 of handpiece 312, an outer shaft 326 extending distally from proximal hub 324, and a cutting shaft 328 extending through outer shaft 326. A proximal end of cutting shaft 328 includes an input interface 329 engaged therewith. End effector assembly 314 further includes a communication device 389, e.g., a RFID tag, storing information regarding end effector assembly 314 such as, for example, identifying information, use setting information, etc., disposed on or within proximal hub 324. Upon engagement of end effector assembly 314 with handpiece 312, communication device 389 is disposed in contact or sufficient proximity relative to communication receiver 321 to enable communication receiver 321 to read information from communication device 389 and relay the same to control console 330 for use in controlling motor 320 to drive end effector assembly 314 in accordance with the settings, parameters, and/or other configuration thereof.

Upon engagement of end effector assembly 314 with handpiece 312, the interior of cutting shaft 328 and/or the interior of outer shaft 326 of end effector assembly 314 is disposed in fluid communication with flow lumen 323 extending through housing 316 of handpiece 312 such that fluid, tissue, and debris drawn into cutting shaft 328 and/or outer shaft 326 may be suctioned, under vacuum, through end effector assembly 314, flow lumen 323 of handpiece, and out proximal connector 325 of handpiece 312 to outflow tubing 380.

Outflow tubing 380 includes a distal end 384 configured to releasably couple to proximal connector 325 of handpiece 312 and a proximal end 386 configured to couple to collection canister 350. Outflow tubing 380 further includes a valve module 382 configured for engagement with, e.g., receipt within, a module dock 322 disposed on control console 330. The connection between valve module 382 and module dock 322 enables control console 330 to control the controllable valve (not shown) of valve module 382 in an appropriate manner, e.g., in accordance with the activation/deactivation of motor 320 of handpiece 312, the position and/or orientation of the cutting shaft 328 of end effector assembly 314, or in any other suitable manner. Valve module 382 and module dock 322 are similar to valve module 282 and module dock 222 (FIG. 2) except that, rather than including communication in addition to valve control as with valve module 282 and module dock 222 (FIG. 2), the communication in surgical system 300 is relocated to between end effector assembly 314 and handpiece 312 (via communication device 389 and communication receiver 321) and, thus, only valve control is provided between valve module 382 and module dock 322.

Surgical system 300 eliminates tubing connected directly to end effector assembly 314 and, thus, simplifies the routing of tubing out of the way of the grasping and manipulation of handpiece 312. Further, as with surgical system 200 (FIG. 2), by providing module dock 322 at control console 330, the need to provide module dock 322 and any associated components on handpiece 312 and/or through cable 370 is obviated. With respect to surgical system 300, it is contemplated that end effector assembly 314 and outflow tubing 380 be configured as single-use, disposable components, while handpiece 312 and control console 330 are configured as reusable components. Collection canister 350 and/or vacuum tubing 390 may be configured as disposable or reusable components in surgical system 300 (and similarly in surgical systems 100, 200 (FIGS. 1 and 2, respectively)).

Figure 4:
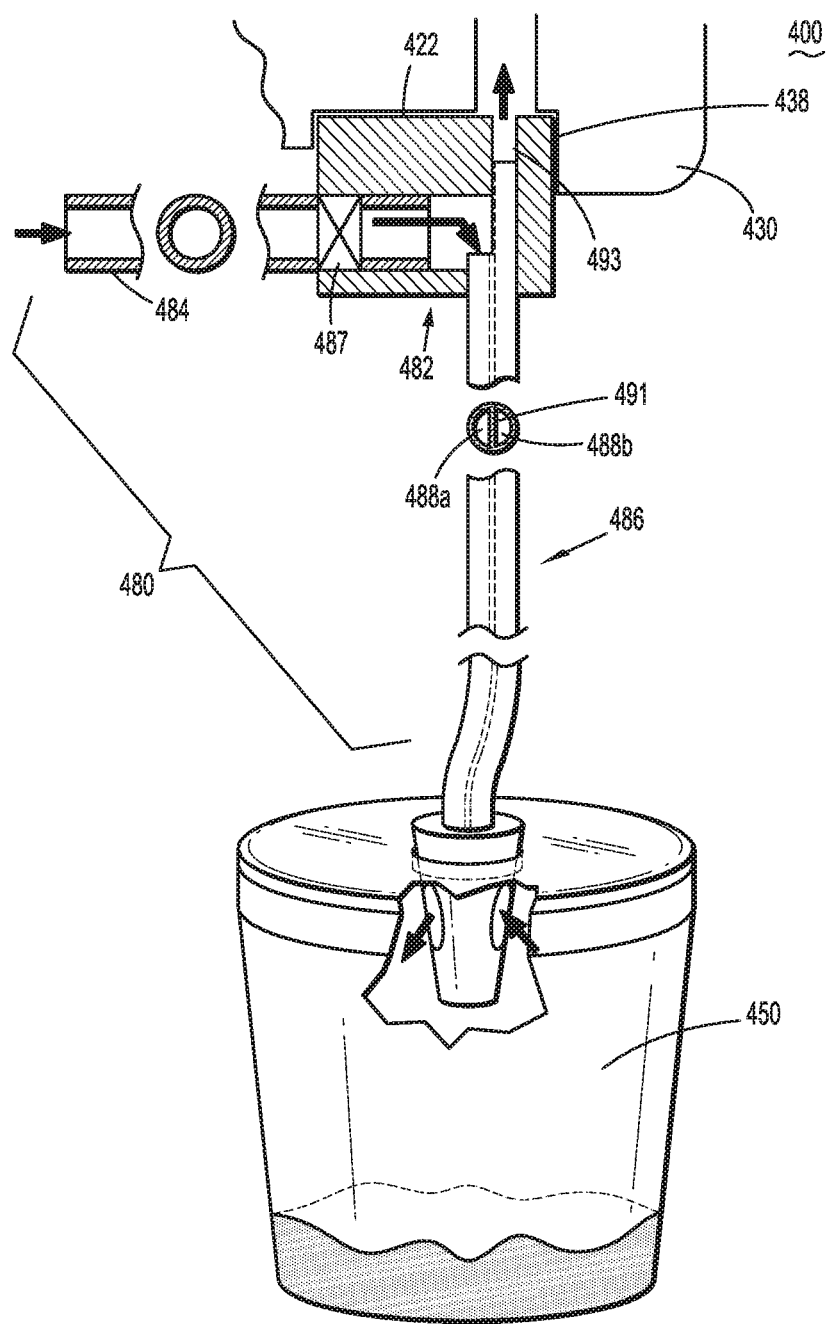
FIG. 4 is a perspective, particular cross-sectional view of a portion of yet another surgical system provided in accordance with aspects of the present disclosure.

With reference to FIG. 4, another surgical system provided in accordance with aspects of the present disclosure is shown generally identified by reference numeral 400. Surgical system 400 generally includes a surgical instrument (not shown, similar to any of the surgical instruments detailed above), a control console 430, and a collection canister 450. Surgical system 400 further includes a cable (not shown, similar to any of the cables detailed above), and tubing 480. Surgical system 400 is similar to and may include any of the features of surgical systems 200 and/or 300 (FIGS. 2 and 3, respectively) except as specifically contradicted below. Thus, for purposes of brevity, only the differences between surgical system 400 and surgical systems 200, 300 (FIGS. 2 and 3, respectively) are described in detail below.

Tubing 480 of surgical system 400 is configured to receive the fluid, tissue, and debris suctioned through the surgical instrument, either directly from the end effector assembly of the surgical instrument as detailed above with respect to surgical system 200 (FIG. 2) or from the end effector assembly via the handpiece of the surgical instrument as detailed above with respect to surgical system 300 (FIG. 3).

Tubing 480 includes a valve module 482 configured for engagement with, e.g., receipt within, a module dock 422 disposed on control console 430. Valve module 482 and control console 430 may be configured to both enable communication and valve control (as with surgical system 200 (FIG. 2)), or may only provide valve control while communication is established elsewhere (as with surgical system 300 (FIG. 3)). In either configuration, tubing 480 further includes a distal tube portion 484 coupled between valve module 482 and the surgical instrument and a proximal tube portion 486 coupled between valve module 482 and collection canister 450 such that tubing 480 defines a flow path from the surgical instrument, through distal tube portion 484, valve module 482, and proximal tube portion 486 into collection canister 450.

Proximal tube portion 486 of tubing 480 includes a multi-lumen configuration. More specifically, proximal tube portion 486 includes first and second isolated flow paths 488a, 488b defined therethrough. First and second flow paths 488a, 488b may be formed from a dividing wall 491 extending through proximal tube portion 486 (as illustrated), via a pair of independent tubes extending through proximal tube portion 486, or in any other suitable manner. First flow path 488a is connected between controllable valve 487 of valve module 482 and collection canister 450 to enable the flow of fluid, tissue, and debris from the surgical instrument into collection canister 450. Second flow path 488b is connected between a vacuum input 493 of valve module 482 and collection canister 450. Vacuum input 493 of valve module 482 is configured to couple to vacuum tube port 438 of module dock 422 of control console 430 and, thus, to the vacuum source (not shown) of control console 430 to establish suction through second flow path 488b and, thus, negative pressure through collection canister 450, first flow path 488a, valve module 482 distal tube portion 484, and the surgical instrument to draw the fluids, tissue, and debris into and through the surgical instrument, tubing 280, and into collection canister 450.

Surgical system 400 as demonstrated above provides a single tubing 480 rather than separate outflow and vacuum tubes, thus simplifying set-up in preparation for use by reducing the number of connections required. More specifically, rather than independently connecting the outflow and vacuum tubing, both the outflow and vacuum tubing are operably coupled with control console 430 and collection canister 450 by connection of valve module 482 with module dock 422 and connection of proximal tube portion 486 of tubing 480 with collection canister 450.

Figure 6:
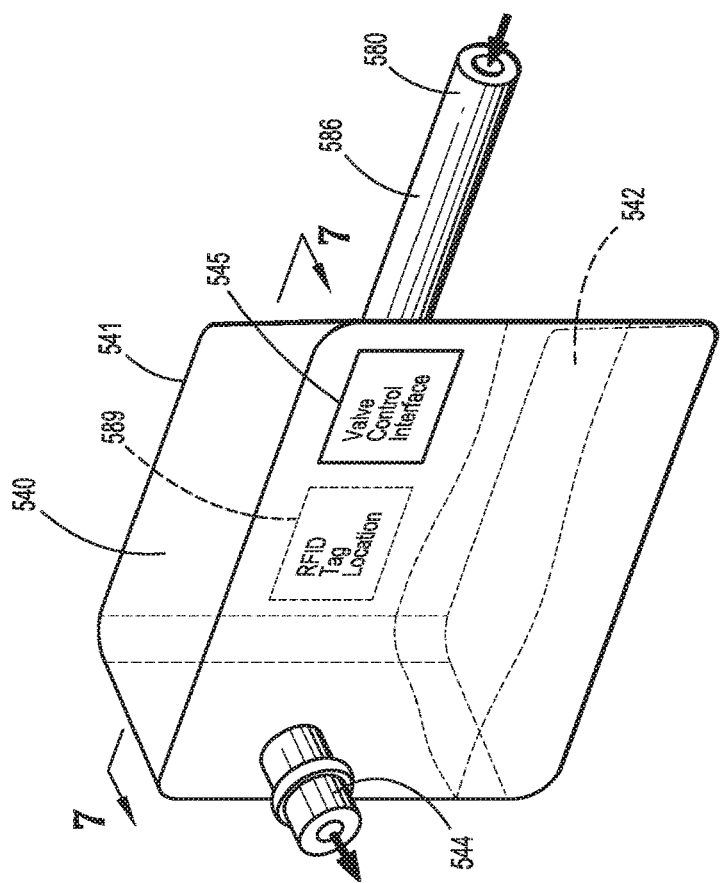
FIG. 6 is a perspective view of a valve and collection module of the surgical system of FIG. 5.
Figure 5:
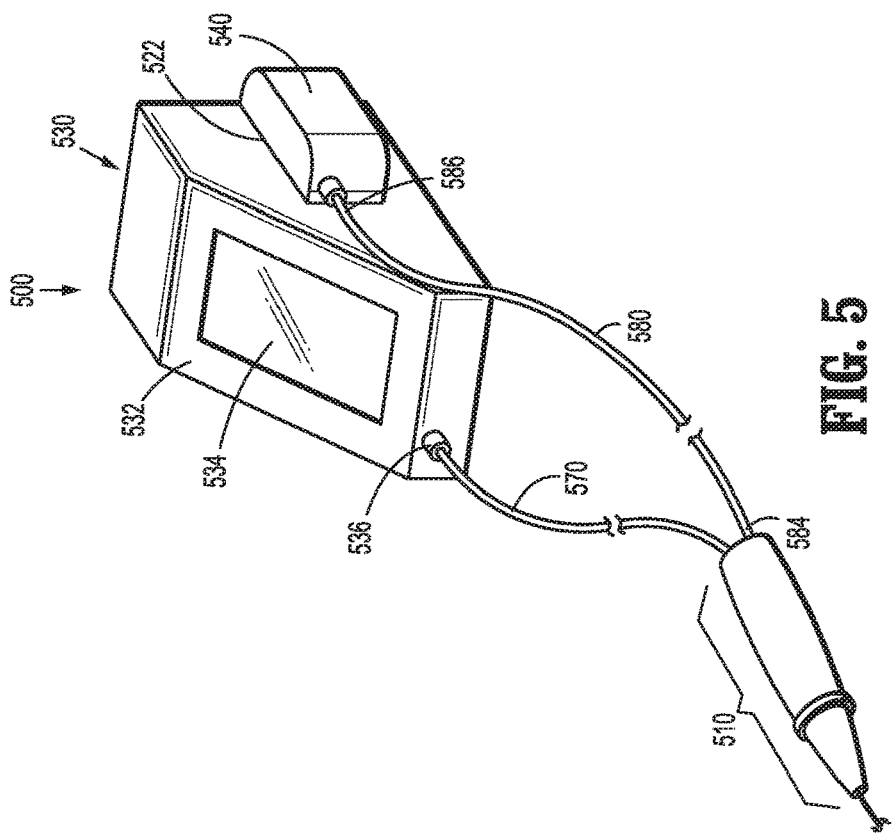
FIG. 5 is a perspective view of still yet another surgical system provided in accordance with aspects of the present disclosure.
Figure 7:
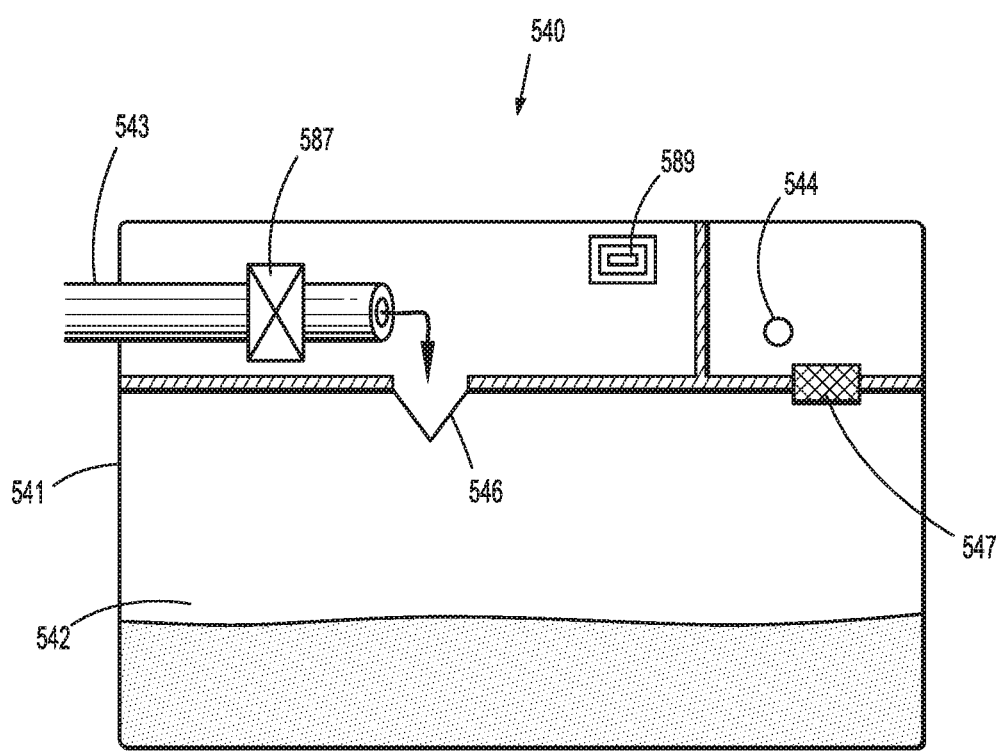
FIG. 7 is a cross-sectional view of taken along section line "7-7" of FIG. 6.

Turning to FIGS. 5-7, another surgical system provided in accordance with aspects of the present disclosure is shown generally identified by reference numeral 500. Surgical system 500 generally includes a surgical instrument 510, a control console 530, and a valve and collection module 540. Surgical system 500 further includes a cable 570 and outflow tubing 580. Surgical instrument 510 may be configured similar to any of the surgical instruments detailed above, e.g., surgical instruments 110, 210, 310 (FIGS. 1-3, respectively). Cable 570 couples surgical instrument 510 and control console 530 to enable control console 530 to power and control operation of the motor (not shown) of surgical instrument 510.

Control console 530 generally includes an outer housing 532, a touch-screen display 534, a cable port 536 configured to receive cable 570, and a module port 522 configured to receive valve and collection module 540, as detailed below. Outer housing 532 houses internal electronics (not shown) as well as a vacuum source (not shown). Control console 530 may otherwise be configured similar to control consoles 130, 230, 330, and/or 430 (FIGS. 1-4, respectively), except as explicitly contradicted herein.

Outflow tubing 580 is configured to receive the fluid, tissue, and debris suctioned through surgical instrument 510, either directly from the end effector assembly of surgical instrument 510 as detailed above with respect to surgical system 200 (FIG. 2) or from the end effector assembly via the handpiece of surgical instrument 510 as detailed above with respect to surgical system 300 (FIG. 3). More specifically, outflow tubing 580 includes a distal end 584 coupled to surgical instrument 510 and a proximal end 586 coupled to valve and collection module 540, and defines a flow path therebetween for delivering fluid, tissue, and debris from surgical instrument 510 to valve and collection module 540.

Valve and collection module 540 includes an outer housing 541, an internal collection reservoir 542, an inflow port 543 configured to receive proximal end 586 of outflow tubing 580, a vacuum port 544 configured to connect to a vacuum port of module port 522 of control console 530, and a communication device 589, e.g., an RFID tag, disposed on or within outer housing 541. In embodiments, proximal end 586 of outflow tubing 580 is fixedly engaged within inflow port 543 of valve and collection module 540 such that valve and collection module 540 and outflow tubing 580 are a single, integrated component. Valve and collection module 540 is configured to releasably mechanically engaged and operably couple with module dock 522 of control console 530 in any suitable manner, e.g., friction fitting, mechanical latching, etc. More specifically, with valve and collection module 540 engaged with module dock 522, valve and collection module 540 is fully supported by control console 530 and maintained in engagement therewith without the need for additional support, e.g., from a support surface, stand, etc. In embodiments, valve and collection module 540 is maintained in a "floating" position, displaced from the support surface supporting control console 530. Alternatively, valve and collection module 540 may be maintained in a position whereby valve and collection module 540 rests upon the support surface supporting control console 530; however, as noted above, the support surface is not needed to maintain the engagement between valve and collection module 540 and control console 530.

Continuing with reference to FIGS. 5-7, a controllable valve 587 of valve and collection module 540 is disposed within inflow port 543. A valve interface 545 (FIG. 6) is operably coupled to controllable valve 587 and configured to electrically and/or mechanically couple to a corresponding interface (not shown) of module dock 522 of control console 530 to enable control console 530 to electrically and/or mechanically control controllable valve 587 in an appropriate manner during use, e.g., as detailed above.

A one-way valve 546 is disposed between inflow port 543 and collection reservoir 542 to enable the passage of fluid, tissue, and debris therethrough into collection reservoir 542 while inhibiting the escape of fluid, tissue, and debris from collection reservoir 542 through one-way valve 546. A barrier 547 is disposed between vacuum port 544 and collection reservoir 542 to enable the application of vacuum therethrough while inhibiting the passage of fluid, tissue, debris therethrough. Upon activation of the vacuum source of control console 530, negative pressure is established through vacuum port 544, collection reservoir 542, inflow port 543, outflow tubing 580, and surgical instrument 510 to draw the fluids, tissue, and debris into and through surgical instrument 510 and into collection reservoir 542.

Communication device 589 of valve and collection module 582 stores information regarding the end effector assembly of surgical instrument 510 such as, for example, identifying information, use setting information, etc. With valve and collection module 582 engaged with module dock 522 of control console 530, the information stored on communication device 589 may be communicated to control console 530 (via a communication receiver, e.g., an RFID reader, of module dock 522) for use in controlling the motor to drive the end effector assembly of surgical instrument 510 in accordance with the settings, parameters, and/or other configuration thereof.

Surgical system 500, as demonstrated above, obviates the need for a separate collection canister and, instead, incorporates collection reservoir 542 into valve and collection module 582, which is configured for mounting on control console 530, thus facilitating set-up in preparation for use and minimizing the number of components required. Surgical system 500 is configured for use in relatively short procedures and/or procedures involving relatively small amount of fluid, as the capacity of collection reservoir 542 is smaller than that of a traditional collection canister.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

Although the foregoing disclosure has been described in some detail by way of illustration and example, for purposes of clarity or understanding, it will be obvious that certain changes and modifications may be practiced within the scope of the appended claims.

What is claimed is:

1. A surgical system, comprising:
   a surgical instrument including an end effector assembly and a handpiece, wherein the surgical instrument includes a module dock arranged in the handpiece, wherein the end effector assembly is separable from the handpiece;
   a collection canister;
   outflow tubing coupled between the end effector assembly and the collection canister to define an outflow path from the end effector assembly to the collection canister, the outflow tubing including a valve module including a controllable valve disposed within the outflow path to selectively control flow along the outflow path, wherein the valve module is arranged along the outflow tubing between the end effector assembly and the collection canister; and
   a control console configured to control operation of the surgical instrument and to control the controllable valve, wherein the module dock is configured to releasably engage the valve module, the control console configured to control the controllable valve via the module dock of the surgical instrument.

2. The surgical system according to claim 1, wherein the valve module further includes a communication device and wherein the module dock is configured to retrieve information from the communication device upon engagement of the valve module with the module dock.

3. The surgical system according to claim 1, further comprising vacuum tubing coupled between the control console and the collection canister.

4. The surgical system according to claim 1, wherein the outflow tubing includes a distal tube portion connected between the surgical instrument and the valve module and a proximal tubing portion connected between the valve module and the collection canister.

5. The surgical system according to claim 4, wherein the valve module further includes an inflow port and a vacuum port, and wherein the proximal tubing portion defines first and second isolated flow paths, the first isolated flow path defined between the inflow port and the collection canister and the second isolated flow path defined between the vacuum port and the collection canister.

6. A surgical system, comprising:
   an end effector assembly;
   a handpiece configured to drive the end effector assembly, wherein the handpiece is separable from the end effector assembly;
   a module dock arranged in the handpiece;
   a collection canister;
   outflow tubing extending from the end effector assembly to the collection canister;
   a valve module arranged along the outflow tubing between the end effector assembly and the collection canister, the valve module including a controllable valve configured to selectively permit or inhibit a flow through the outflow tubing;
   a control console configured to control operation of the end effector assembly, the handpiece, and the controllable valve; and
   a cable connecting the handpiece with the control console, wherein the module dock is configured to releasably engage the valve module, the control console configured to control the controllable valve via the module dock of the handpiece.

7. The surgical system of claim 6, further including a vacuum tubing extending between the control console and the collection canister, the control console configured to generate negative pressure in the collection canister by drawing air through the vacuum tubing.

8. The surgical system according to claim 6, wherein the module dock is configured to communicate information about the end effector assembly to the control console.

9. The surgical system according to claim 6, wherein the module dock is configured to communicate information about the outflow tubing to the control console.

10. The surgical system according to claim 6, wherein the valve module further includes a communication device, and wherein the module dock is configured to retrieve information from the communication device upon engagement of the valve module with the module dock.

11. The surgical system according to claim 10, wherein the communication device includes an RFID (radio frequency identification) tag.

12. The surgical system according to claim 11, wherein the RFID tag stores information regarding the end effector assembly.

13. The surgical system according to claim 6, wherein the handpiece includes a motor, and the end effector assembly includes a shaft, the motor of the handpiece configured to drive the shaft of the end effector assembly.

14. The surgical system according to claim 13, wherein the control console is configured to power and control the motor of the handpiece to drive the shaft of the end effector assembly.

* * * * *